United States Patent [19]

Shiranita et al.

[11] Patent Number: 5,495,176

[45] Date of Patent: Feb. 27, 1996

[54] CERAMICS CELL FOR MEASURING ELECTRICAL CONDUCTIVITY OF LIQUID SOLUTION

[75] Inventors: Akira Shiranita, Okayama; Susumu Nakayama, Bizen, both of Japan

[73] Assignee: Shinagawa Refractories Co., Ltd., Tokyo, Japan

[21] Appl. No.: 350,668

[22] PCT Filed: Jul. 31, 1992

[86] PCT No.: PCT/JP92/00974

§ 371 Date: Apr. 2, 1993

§ 102(e) Date: Apr. 2, 1993

[87] PCT Pub. No.: WO93/03354

PCT Pub. Date: Feb. 18, 1993

Related U.S. Application Data

[63] Continuation of Ser. No. 30,367, Apr. 2, 1993, abandoned.

[30] Foreign Application Priority Data

Aug. 6, 1991 [JP] Japan ................................ 3-196528

[51] Int. Cl.$^6$ ............................................. G01N 27/42
[52] U.S. Cl. ............................ 324/439; 324/450; 204/422
[58] Field of Search ................................... 324/439, 446, 324/447, 450, 663, 696; 204/243 R, 244, 279, 291, 297 R, 404, 422, 428, 429; 429/176

[56] References Cited

U.S. PATENT DOCUMENTS

| | | | |
|---|---|---|---|
| 3,593,119 | 7/1971 | Brum et al. | 324/439 |
| 4,046,661 | 9/1977 | Stringer et al. | 204/422 |
| 5,025,219 | 6/1991 | Gaspard | 324/447 |
| 5,151,660 | 9/1992 | Powers et al. | 324/663 X |
| 5,186,806 | 2/1993 | Clark et al. | 204/429 X |
| 5,187,444 | 2/1993 | Kumada et al. | 324/663 |

FOREIGN PATENT DOCUMENTS

| | | |
|---|---|---|
| 0193015A2 | 9/1986 | European Pat. Off. . |
| 0401724A2 | 12/1990 | European Pat. Off. . |
| 0380752A1 | 8/1992 | European Pat. Off. . |

*Primary Examiner*—Kenneth A. Wieder
*Assistant Examiner*—Diep Do
*Attorney, Agent, or Firm*—Armstrong, Westerman, Hattori, McLeland & Naughton

[57] ABSTRACT

In a cell for measuring electrical conductivity, a container (2) and electrodes (1) are made of ceramics having high corrosion-resistant property. Insulating ceramics are used for the container (2), and conductive ceramics having resistance value of several k$\Omega$.cm or less is used for the electrodes (1). The ceramics are far superior to glass in corrosion resistant property and mechanical strength under normal as well as high temperature conditions. Further, the cell is produced at lower cost than the one made of precious metal and has high corrosion resistant property and can be used under strong acid or strong alkaline conditions. It has high mechanical strength and can be used under high pressure and high temperature conditions and produced at low cost because precious metal is not used for the electrodes.

7 Claims, 5 Drawing Sheets

Fig. 3

| CONDITIONS | | CONTAINER MATERIAL (INSULATING CERAMICS) | ELECTRODE MATERIAL (CONDUCTIVE CERAMICS) | | |
|---|---|---|---|---|---|
| CHEMICALS | TEMP. | α-SIALON | 1 α-SIALON-TiN | 2 α-SIALON-TiC | 3 α-SIALON-SiC |
| H₂SO₄ (CONC.) | 80°C | 0.04 | -0.47 | -0.04 | 0.01 |
| H₂SO₄ (10%) | 80°C | 0.82 | 1.05 | 1.11 | 0.30 |
| HCl (CONC.) | 80°C | 0.37 | 2.55 | 2.20 | 0.52 |
| HCl (10%) | 80°C | 0.57 | 2.35 | 2.10 | 0.51 |
| HNO₃ (CONC.) | 80°C | 0.14 | 0.54 | 0.72 | 0.02 |
| HNO₃ (10%) | 80°C | 0.55 | 4.53 | 3.23 | 0.81 |
| HF (5%) | ROOM TEMP. | 0.33 | 0.78 | 0.84 | 0.25 |
| NaOH (50%) | 80°C | 0.07 | 0.01 | 0.02 | 0.00 |

UNIT: WEIGHT DECREASE (mg/cm² · DAY)

| | | 3-POINT MODULUS OF RUPTURE (kg/mm²) | FRACTURE TOUGHNESS (MN/m^{1/2}) |
|---|---|---|---|
| CONTAINER MATERIAL (INSULATING CERAMICS) | α-SIALON | 100 | 6 |
| ELECTRODE MATERIAL (CONDUCTIVE CERAMICS) | 1 α-SIALON-TiN | 75 | 5 |
| | 2 α-SIALON-TiC | 75 | 6 |
| | 3 α-SIALON-SiC | 80 | 5 |

Fig. 4

| CONTAINER MATERIAL (INSULATING CERAMICS) | | α-SIALON | ELECTRIC RESISTANCE (Ω·CM) |
|---|---|---|---|
| | | | $10^{12}$ OR MORE |
| ELECTRODE MATERIAL (CONDUCTIVE CERAMICS) | 1 | α-SIALON-TiN | $10^1$ OR LESS |
| | 2 | α-SIALON-TiC | $10^3$ OR LESS |
| | 3 | α-SIALON-SiC | $10^3$ OR LESS |

Fig. 5

CERAMICS CELL FOR MEASURING ELECTRICAL CONDUCTIVITY OF LIQUID SOLUTION

This application is a continuation of application Ser. No. 08/030,367 filed Apr. 2, 1993, now abandoned.

TECHNICAL FIELD

The present invention relates to a cell for measuring electrical conductivity of liquid having conductivity of 100 k $\Omega$.cm or less, and in particular to a cell for measuring conductivity, which can be used at high temperature or high pressure conditions and in corrosive substances by adopting ceramics for container and electrodes.

BACKGROUND TECHNIQUE

In the past, a cell as shown in FIG. 1 has been used for measuring electrical conductivity of liquid having conductivity of 100 k $\Omega$.cm or less.

FIG. 1(a) shows a cell, which comprises a glass container 2 with side tubes 4 protruding inwardly on the sides thereof, electrodes 1 made of precious metal such as platinum and supported on tips of the side tubes, and lead wires 5 passed through the side tubes.

Specimen liquid 6 is placed in the container and a stopper 3 is provided to close it, and electric current is applied across the electrodes to measure electrical conductivity.

FIG. 1(b) shows a filling type cell for laboratory use. On both ends of an oblong glass container 2, electrodes 1 are disposed, and specimen liquid is filled through and discharged from two side tubes 7a and 7b extending upward. By applying electric current across the electrodes on the two ends of the glass container 2, electrical conductivity is measured.

FIG. 1(c) shows an immersion type cell. A glass container 2 has a small opening. By immersing the container in specimen liquid, the liquid enters through the opening. Electrical conductivity is measured by applying electric current across the electrodes.

However, each of the conventional type cells has a problem in corrosion resistant property, particularly against alkali, because glass is used for the container. Also, there are problems with mechanical strength and corrosion resistant property under high temperature and high pressure conditions. If metal other than precious metal is used for electrodes, problems arise with corrosion resistant property. The use of precious metal leads to the increase of cost because Pt, Au, etc. are expensive.

It is an object of the present invention to provide a cell, which has high corrosion resistant property and can be used under strong acid or strong alkaline conditions.

It is another object of the present invention to provide a cell, which has high mechanical strength and is suitable for the use under high pressure and high temperature conditions.

It is still another object of the present invention to provide a cell, which can be produced at lower cost.

DISCLOSURE OF THE INVENTION

To attain the above objects, the cell for measuring conductivity according to the present invention uses ceramics with high corrosion resistant property for container and electrodes, whereby the container is made of insulating ceramics, and electrodes are made of conductive ceramics having resistance value of several k $\Omega$.cm or less.

As ceramic materials for electrodes, there are carbides such as TiC, ZrC, VC, TaC, $Mo_2C$, WC, SiC, etc., nitrides such as TiN, ZrN, VN, NbN, TaN, $Cr_2N$, etc., carbonitride Ti(C-N), borides such as $TiB_2$, $ZrB_2$, $NbB_2$, $TaB_2$, $CrB_2$, MoB, etc., silicides such as $TiSi_2$, $ZrSi_2$, $NbSi_2$, $CrSi_2$, $MoSi_2$, $WSi_2$, etc., single conductive ceramic such as $TiO_{2-x}$, conductive material such as complex ceramics containing two or more types of these substances, oxynitrides type sialon (a series of substances containing elements of Si-Al-O-N), and complex ceramics with $Al_2O_3$, $ZrO_2$, etc.

As the ceramic materials to be used for the container, there are various types of insulating ceramics such as $Si_3N_4$, $\alpha$-sialon($Y_x(Si,Al)_{12}(O,N)_{16}$), $\beta$-sialon ($Si_{6-z}Al_zN_{8-z}O_z$), $ZrO_2$, $Al_2O_3$, mullite, spinel, SiC, etc.

With the materials selected from these substances, a cell in cylindrical shape is prepared as shown in FIG. 2. In FIG. 2, the reference numeral 1 represents an electrode made of conductive ceramics, 2 is a container made of insulating ceramics, and the electrodes are provided on the sides of the container. To produce such cell, there are various methods such as a method to integrally mold two types of powder materials for container and electrodes and to fabricate and fire, a method to mold the container and the electrodes separately and then to combine them and to fire, a method to mold and fire the container and the electrodes separately and bond with glass-frit having high corrosion resistant property.

The present invention provides a cell for conductivity measurement, which comprises container and electrodes made of ceramics. The ceramics are much superior to glass in corrosion resistant property and mechanical strength under normal as well as high temperature conditions and are less expensive than precious metal. Therefore, the cell for measuring conductivity of the present invention has high corrosion resistant property and can be used under strong acid or strong alkaline conditions. It is also suitable for the use under high pressure and high temperature conditions because it has high mechanical strength. Further, it can be produced at low cost because precious metal is not used for the electrodes. The junction between the container and the electrodes has airtightness as high as $10^{-7}$ Torr or more by He leakage test, and there is no possibility of liquid leakage.

BRIEF DESCRIPTION OF THE DRAWINGS

FIG. 3 shows the results of chemical resistance test;

FIG. 4 summarizes mechanical property of the materials; and

FIG. 5 shows electric resistance values of the materials.

BEST MODES FOR CARRYING OUT THE INVENTION

Figure 1A:
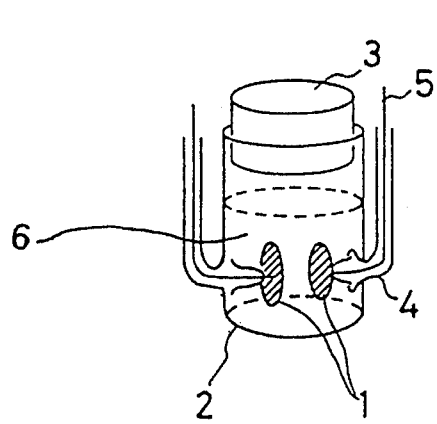
FIG. 1(a–c) illustrates conventional type cells for measuring conductivity.
Figure 1B:
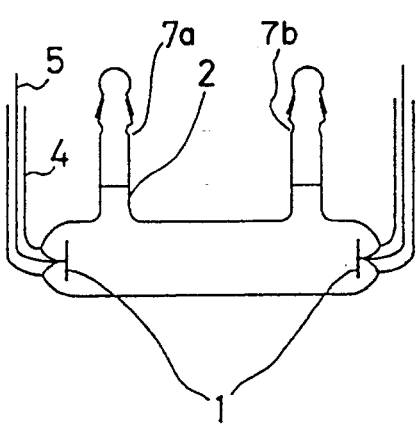
Figure 1C:
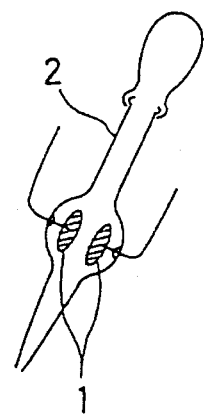
Figure 2:
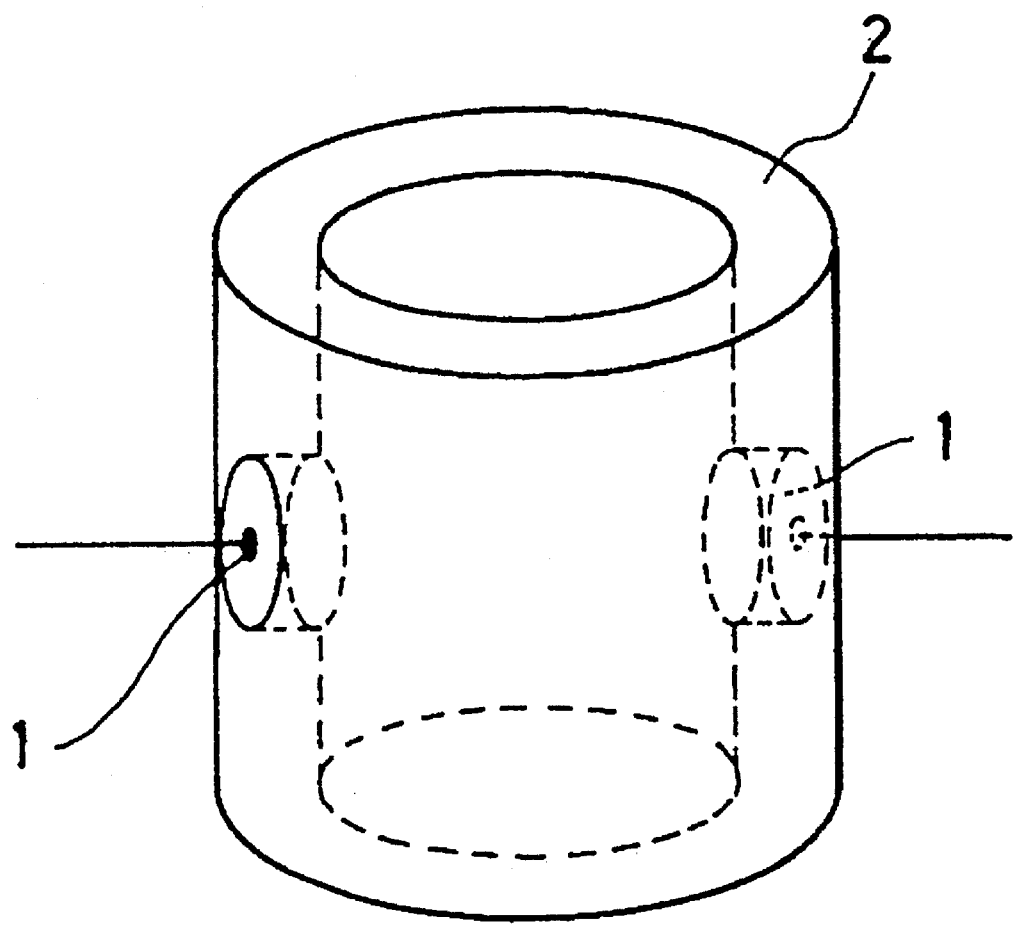
FIG. 2 shows a cell for measuring conductivity of the present invention.

FIG. 2 represents an embodiment of a cell for measuring conductivity according to the present invention. $\alpha$-sialon is used as insulating ceramics for the container portion 2. As conductive ceramics for the electrodes 1, (1) TiN-dispersed $\alpha$-sialon, (2) TiC-dispersed $\alpha$-sialon, and (3) SiC-dispersed $\alpha$-sialon are used. To prepare raw material powder for the insulating $\alpha$-sialon, $Si_3N_4$, $Y_2O_3$ and AlN were blended by weight ratio of 91:5:4, and the mixture was kneaded in a ball mill for 48 hours with ethanol and was dried. The raw material powder of conductive α-sialon-TiN in (1) above was prepared by blending $Si_3N_4$, $Y_2O_3$, AlN and TiN by weight ratio of 54:3:2:41, the raw material powder of the conductive α-sialon-TiC of (2) above was prepared by blending $Si_3N_4$, $Y_2O_3$, AlN, TiC and $Al_2O_3$ by weight ratio of 54:3:2:40:1, and the raw material powder of the conductive α-sialon-SiC of (3) above was prepared by blending $Si_3N_4$, $Y_2O_3$, AlN, SiC and carbon black by weight ratio of 54:3:2:40:1. Each of these mixtures was kneaded in a ball mill for 48 hours with ethanol and was dried. The raw material powder thus prepared was processed by CIP molding at 1,000 kg/cm$^2$ and was fired for 2 hours at 1,600°–1,950° C. in nitrogen atmosphere to produce sintered substance. The results of chemical resistance test, mechanical property, and electric resistance values of each of the sintered substances of α-sialon, (1) α-sialon-TiN, (2) α-sialon-TiC, and (3) α-sialon-SiC are given in FIG. 3, FIG. 4 and FIG. 5 respectively.

FIG. 3 shows the results of chemical resistance test. When the materials were exposed to $H_2SO_4$, HCl, $HNO_3$ (concentration: conc. and 10%; temperature: 80° C.), HF (room temperature), and NaOH (concentration: 50%; temperature: 80° C.), weight decrease (mg/cm$^2$.day) was slight, and it is evident that each of these materials has very high corrosion resistant property.

FIG. 4 gives 3-point modulus of rupture (kg/mm$^2$) and fracture toughness (MN/m$^{1/2}$) of container material (insulating ceramics) and electrode material (conductive ceramics). It is evident that the materials have very high mechanical strength.

FIG. 5 shows electric resistance values (Ω.cm) of the materials. From the figure, it is evident that the container material has resistance value as high as $10^{12}$ or more, while the electrode material has resistance of 10 or less, showing excellent conductivity. The resistance value may be less than several k Ω.cm.

EXAMPLE 1

Each of the raw material powders of α-sialon, (1) α-sialon-TiN, (2) α-sialon-TiC, or (3) α-sialon-SiC was processed by CIP molding under pressure of 500–1,000 kg/cm$^2$. Then, as shown in FIG. 2, α-sialon material was molded into the shape of the container, the materials of (1) α-sialon-TiN, (2) α-sialon-TiC, and (3) α-sialon-SiC were molded into the shape of electrodes, and these were combined together. By sintering the base materials for 2 hours at 1,600°–1,950° C. in nitrogen atmosphere, the cell for conductivity measurement was obtained. The container and the electrodes were bonded closely without gap, and airtightness was as high as $10^{-7}$ Torr or more by He leakage test.

EXAMPLE 2

Each of the raw material powders of α-sialon, (1) α-sialon-TiN, (2) α-sialon-TiC, or (3) α-sialon-SiC was processed by CIP molding under pressure of 1,000 kg/cm$^2$. Then, as shown in FIG. 2, α-sialon material was molded into the shape of the container, and the materials of (1) α-sialon-TiN, (2) α-sialon-TiC, or (3) α-sialon-SiC were molded into the shape of electrode, and these were sintered for 2 hours at 1,600°–1,950° C. in nitrogen atmosphere. The sintered materials thus obtained were fabricated in such manner that clearance was 0.1 mm or less when the container and the electrodes were assembled and bonded at 1,000° C. in nitrogen atmosphere using glass having high chemical resistance such as borosilicate frit or titanium frit. The cell thus obtained showed airtightness as high as $10^{-7}$ Torr or more between the container and the electrodes by He leakage test, similarly to Example 1.

INDUSTRIAL APPLICABILITY

As described above, the cell for measuring conductivity according to the present invention has high corrosion resistant property and is suitable for the use under strong acid or strong alkaline conditions. Because it has high mechanical strength, it can be used under high pressure and high temperature conditions. Further, it can be produced at low cost because precious metal is not used for the electrodes. Thus, the cell is very valuable in industrial applications.

What is claimed is:

1. A cell for measuring electrical conductivity of a specimen, comprising a container for holding the specimen, the container provided with two electrodes in spaced relationship from each other within the container, the electrodes and the container being integrally molded together, the electrodes contacting the specimen such that electric current is applied across the two electrodes to measure electrical conductivity, wherein the container is made of insulating ceramics and the electrodes are made of conductive ceramics.

2. A cell for measuring electrical conductivity according to claim 1, wherein the electrodes are made of conductive ceramics having resistance value of several k Ω.cm or less.

3. A cell for conductivity according to claim 2, wherein the conductive ceramic materials contain carbides such as TiC, ZrC, VC, TaC, $Mo_2C$, WC, SiC, etc., nitrides such as TiN, ZrN, VN, NbN, TaN, $Cr_2N$, etc., carbonitride Ti (C-N), borides such as $TiB_2$, $ZrB_2$, $NbB_2$, $TaB_2$, $CrB_2$, MoB, etc., silicides such as $TiSi_2$, $ZrSi_2$, $NbSi_2$, $CrSi_2$, $MoSi_2$, $WSi_2$, etc., single conductive ceramic such as $TiO_{2-x}$, conductive materials such as complex ceramics containing two types or more of these substances, and complex ceramics with $Si_3N_4$, sialon, $Al_2O_3$, $ZrO_2$, etc.

4. A cell for measuring electrical conductivity according to claim 2, wherein the insulating ceramic material contains various types of ceramic material such as $Si_3N_4$, α-sialon, β-sialon, $ZrO_2$, $Al_2O_3$, mullite, spinel, SiC, etc.

5. A cell for measuring electrical conductivity according to claim 1, wherein a junction between the container and the electrodes has air tightness of $10^{-7}$ Torr or more.

6. A cell for measuring electrical conductivity according to claim 1, wherein the specimen is a liquid having a conductivity of 100 k Ω.cm or less.

7. A cell for measuring electrical conductivity according to claim 1, wherein the container has a cylindrical shape and the electrodes are provided on the sides of the container.

* * * * *